US00PP25594P2

(12) United States Plant Patent
van den Top

(10) Patent No.: US PP25,594 P2
(45) Date of Patent: May 26, 2015

(54) ***HOSTA* PLANT NAMED 'BRIDAL FALLS'**

(50) Latin Name: ***Hosta* hybrid (Tratt.)**
Varietal Denomination: Bridal Falls

(71) Applicant: Henrik Jan van den Top, Barneveld (NL)

(72) Inventor: Henrik Jan van den Top, Barneveld (NL)

(73) Assignee: Walters Gardens, Zeeland, MI (US)

( * ) Notice: Subject to any disclaimer, the term of this patent is extended or adjusted under 35 U.S.C. 154(b) by 272 days.

(21) Appl. No.: 13/986,082

(22) Filed: Mar. 29, 2013

(51) Int. Cl.
*A01H 5/12* (2006.01)

(52) U.S. Cl.
USPC ..... Plt./353

(58) Field of Classification Search
CPC ..... A01H 5/12; A01H 5/00; A01H 5/02
USPC ..... Plt./353
See application file for complete search history.

*Primary Examiner* — June Hwu

(57) ABSTRACT

The new and distinct *Hosta* plant named *Hosta* 'Bridal Falls' with cordate leaves having blue-green centers and wide yellow margins that develop into a creamy white to white margins. Flowers are light lavender on large-sized plant held attractively above the variegated foliage.

1 Drawing Sheet

Botanical classification: *Hosta* hybrid (Tratt.).
Variety denomination: 'Bridal Falls'.

BACKGROUND OF THE INVENTION

The present invention relates to the new and distinct *Hosta* plant, *Hosta* 'Bridal Falls' discovered by Hendrik Jan van den Top at a nursery in Barneveld, The Netherlands in the summer of 2009 as an uninduced whole plant mutation in a tissue cultured crop of *Hosta* 'Niagara Falls' (not patented). The new plant has been successfully asexually propagated by division at a nursery in Zeeland, Mich. and by sterile plant tissue culture, and in both asexual propagation systems found to be stable and produce identical plants that maintain the unique characteristics of the original plant.

BRIEF SUMMARY OF THE INVENTION

*Hosta* 'Bridal Falls' differs from its sport parent, 'Niagara Falls', as well as all other *hostas* known to the applicant. Other similar varieties include: *Hosta* 'Crispula' (not patented), 'Gone with the Wind' (not patented), 'Lonesome Pine' (not patented), 'Silk Kimono' (not patented), 'Zippity Do Dah' (not patented. 'Crispula' has a longer and more pointed leaf shape, the margin emerges whiter and the flowers are paler lavender. 'Gone with the Wind' leaves are less arching in maturity, less sinuate or undulate in the margin and longer and more pointed than the new variety. 'Lonesome Pines' is also less arching foliage, the leaf apex is less acute and leaf margin less sinuate. 'Silk Kimono' has fewer leaf vein pairs that are also less pronounced or less impressed and less sinuate margins. 'Zippity Do Dah' has more elongated and narrower leaves with fewer vein pairs and the leaf blade is more coarsely sinuate rather than the intense undulations confined to the leaf margins. All of the above cultivars have green leaf centers with white to creamy-yellow margins having margins or coarse waves throughout the leaf blades, but 'Bridal Falls' has a more intense sinuate or rippled (piecrusting) margin with the reminder of the leaf flat except for the intensely impressed veins. 'Bridal Falls' differs from its mutation parent, 'Niagara Falls', by having a broad creamy yellow margin upon leaf emergence that develops to a creamy-white to white.

There are over 4,950 cultivars registered with The American *Hosta* Society, which is the International Cultivar Registration Authority for the genus *Hosta* and a similar number of unregistered cultivars. *Hosta* 'Bridal Falls' differs from all these registered and unregistered cultivars known to the inventor in the following combined traits:

1. Plant of large size with foliage that arches over in maturity.
2. Cordate leaves with green centers and sinuate or undulate margins of creamy yellow margins upon leaf emergence that develops to a creamy white to white.
3. Foliage has deeply impressed veins above and sharply ridged veins below.
4. Numerous light-lavender slightly pendulous flowers on erect scapes well above foliage with large bracts below each flower having similar color to flowers.

BRIEF DESCRIPTION OF THE DRAWINGS

The photographs of the two-year old plant demonstrate the overall appearance of the plant, including the unique traits, grown in a partially shaded greenhouse in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
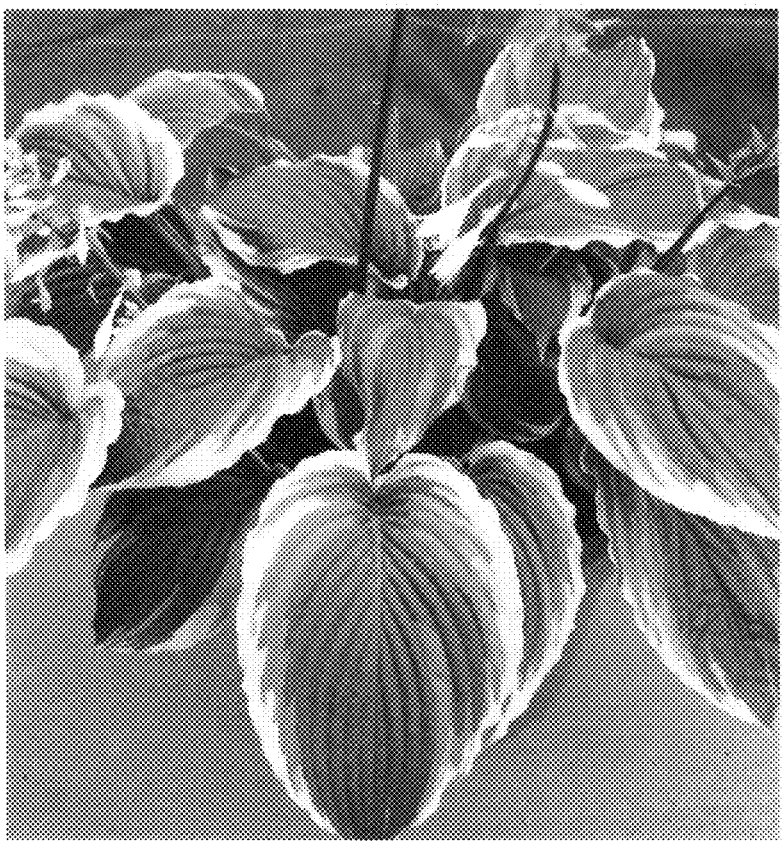
FIG. 1 shows a leaf close-up of a two-year old plant in the early part of the growing season.
Figure 2:
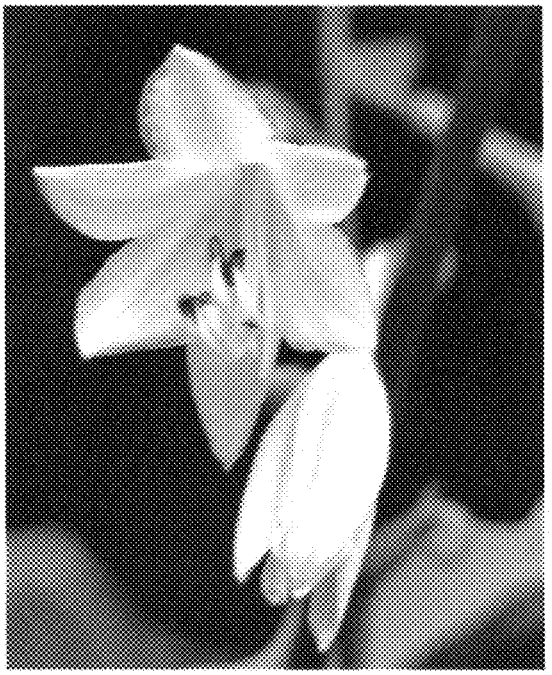
FIG. 2 shows a close-up of the flower in early August.

The following descriptions and color references are based on the 2001 edition of The Royal Horticultural Society Colour Chart except where common dictionary terms are used. The new plant, *Hosta* 'Bridal Falls', has not been observed under all possible environments. The phenotype may vary slightly with different environmental conditions, such as temperature, light, fertility, growth rate, moisture and specimen maturity, but without any change in the genotype. The following observations and size descriptions are of a two-year old plant in a greenhouse in Zeeland, Mich. with white plastic glazing and light fertilizer.

Botanical classification: *Hosta* hybrid.

Mutation parentage: *Hosta* 'Niagara Falls' (not patented).

Propagation method: By sterile laboratory tissue culture propagation and garden division.

Growth rate: Rapid.

Crop time: Under normal spring growing conditions 8 to 10 weeks to finish in a 4.0-liter container from a 65 mm liner.

Time to initiate roots from tissue culture: About two and a half weeks.

Plant description:

*Plant shape and habit*.—Hardy, long-lived, herbaceous perennial, densely rhizomatous, forming a large mounded clump in maturity, with basal rosette of arching leaves on long petioles; usually radially symmetrical.

*Roots*.—Normal, fleshy, lightly branching, cream-colored in normal soil.

*Plant size*.—Foliage height about 28 cm tall; width of plant at the widest point is approximately 75 cm at the widest point just above soil line.

Foliage description:

*Leaf blade*.—Cordate, entire margins, cordate leaf base with acute apex, flat, mostly bilaterally symmetrical, sinuous or pie-crust margins, with deeply impressed adaxial veins and ribbed abaxial; length to width ratio of about 1.5:1.0; average about 30 cm long and 20 cm wide; 12 to 14 pairs of major parallel veins and one main center vein; glabrous; adaxial (top) surface glaucous becoming dull matte-surfaced late in growing season, abaxial surface (bottom) highly glaucous remaining throughout growing season; margin variegation width portion increasing with maturity from year to year; width of variegation irregular with jetting of intermediate portion; on younger plant lightest margin color average of about 8.0 mm and on older plant average of about 12.0 mm.

*Blade color*.—Early season as emerging adaxial (top) center between RHS 138A and RHS 138B, adaxial margin more yellow than RHSN145D and more green than RHS 160B, intermediate colors of RHS 145B, nearest RHS 138D and nearest RHS 144D in small irregular and linear patches between the margin and center; early season as emerging abaxial (bottom) center more yellow than RHS 138A and more green than RHS 147B, abaxial margin more green than RHS 11B and more yellow than RHS 162D, intermediate colors of nearest RHS 145C and nearest RHS 148D in large irregular and linear patches between the margin and center; mid-season and later adaxial center nearest RHS 137A, creamy-white margin nearest but lighter than RHS 155D and large and small irregular intermediate patches of nearest RHS 147D and other smaller intermediate patches of nearest RHS 145D, lighter and greener than RHS 148C and lighter than RHS 153D; mid-season and later abaxial center nearest RHS N138B, creamy margins nearest but lighter than RHS 155D and large and small irregular intermediate patches or striations of nearest RHS 145A, RHS N144A, RHS 151C and RHS 154D.

*Veins*.—12 to 14 pairs of major parallel veins, with one major center vein; veins impressed above and ridged below to a depth of about 3.0 mm.

*Vein color*.—On early season adaxial center nearest RHS 138A and nearest RHS 145C in the margin; abaxial margin and center the same color as the surrounding leaf tissue.

*Petioles*.—Typically mostly flat entire, concavo-convex, glabrous, glaucous, upright to arching; about 26 to 32 cm long and about 1.2 cm wide measured at 3 cm above soil line.

*Petiole color*.—Margins of petiole same as the respective adaxial blade margins in early season and mid to late season; adaxial and abaxial center between RHS 138C and RHS 138B and lighter than RHS 155D in the margin portion of both surfaces.

Flower description:

*Buds*.—Clavate, bluntly acute to rounded apex with longer thin base; one day prior to opening about 8.0 cm long and 1.7 cm wide at the broadest portion.

*Bud color*.—Lighter than RHS 85D at proximal fused base and lighter still to near white with very slight tinting of RHS 85D at the distal end.

*Flowers*.—Closely arranged, 26 to 38 per scape; each subtended by bract; funnelform; about 5.5 cm wide and 8.0 cm long, (distal flowers slightly smaller); remain open for a normal period, usually one to two days on or cut from plant; scapes remain effective from late-June into mid-July in Zeeland, Mich.; no detectable fragrance.

*Tepals*.—Two sets of three fused at the basal two thirds; acute apex; margins entire; glabrous, approximately 8.0 cm long and 1.5 cm wide.

*Tepal color*.—Abaxial tepal color lighter than RHS 85D; adaxial tepal center middle portion nearest RHS 84C with adaxial margins near white, lighter than RHS N155D in outer 1.0 to 2.0 mm, the adaxial inner tepals having a clear transparent edge of about 1.0 mm wide.

*Gynoecium*.—Single. Style: about 8.5 cm long, 1 mm diameter, curled slightly upward in the distal 1.5 mm; color lighter (more white) than RHS 155D the with the proximal 1.5 mm nearest RHS 145D; Stigma: globose; 1 mm to 2 mm in diameter, color lighter than RHS 155D; Ovary: oval, about 6 mm long and 3 mm diameter; between RHS 145A and RHS 145B.

*Androecium*.—Six. Filaments: six, about 1.0 mm in diameter and 6.8 cm long, shorter than gynoecium; with slight curve upward the proximal 1.5 mm; lighter than RHS 11D throughout; Anthers: oblong; attached midpoint lengthwise; dehiscing along the center longitudinal axis; about 4.0 mm long and 1.5 mm wide, color nearest after anthesis; Pollen: elliptical, less than 0.1 mm long, nearest RHS 13B.

*Bracts*.—Subtending each flower, lanceolate, margins entire, glaucous, glabrous, concavo-convex, widest at middle and tapering to acute apex; sessile, clasping about ½ peduncle; protruding upward about 70 to 80 degree angle away from scape at time of flower opening; size of lowest bract about 8.0 cm long and 1.2 cm wide before first flower, progressively decreasing in both length and width; drying as flowers open.

*Bract color*.—Lowest two or three bracts same color and variegation as foliage; distal bracts lighter than RHS 138D with tinting of nearest RHS 186D most heavily concentrated toward apex; after flower drop and before drying developing to nearest RHS N144D.

*Pedicel*.—Rounded, slightly curved, glaucous, glabrous; about 12 mm long, 3 mm diameter.

*Pedicel color*.—Nearest RHS 186D with a tint of RHS 138C.

*Peduncle*.—Cylindrical, glaucous, glabrous, typically unbranched; usually one per division, mostly upright to slightly arching to about 15 degrees from vertical; about 8 to 10 mm diameter at base, about 75 to 85 cm tall.

*Peduncle color*.—Nearest RHS 137A.

Fruit: Has not yet been observed.

Seeds: Have not yet been observed.

Disease and pest resistance: Disease or pest resistance beyond that common to *hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *hostas*.

I claim:

1. A new and distinct ornamental *Hosta* plant named 'Bridal Falls' as herein described and illustrated, with cordate leaves having dark green centers and wide creamy yellow margins that develop into a creamy white to white, light lavender flowers on large-sized plant, suitable as a potted plant, for landscaping the garden, and for cut flower or leaf arrangements.

* * * * *